United States Patent
De Koster et al.

(10) Patent No.: US 9,925,288 B2
(45) Date of Patent: Mar. 27, 2018

(54) METHOD FOR REMOVING PARTICULATE MATTER IN INDOOR ENVIRONMENTS

(71) Applicant: Living Technologies, Cooperative Vennootschap Met Beperkteaansprakelijkheid, Opwijk (BE)

(72) Inventors: Koen De Koster, Opwijk (BE); Filip Willocx, Heverlee (BE)

(73) Assignee: Living Technologies, Cooperatieve Vennootschap Met Beperkteaansprakelijkheid, Opwijk (BE)

( * ) Notice: Subject to any disclaimer, the term of this patent is extended or adjusted under 35 U.S.C. 154(b) by 0 days.

(21) Appl. No.: 14/408,492

(22) PCT Filed: Jun. 19, 2013

(86) PCT No.: PCT/BE2013/000033
§ 371 (c)(1),
(2) Date: Dec. 16, 2014

(87) PCT Pub. No.: WO2013/188933
PCT Pub. Date: Dec. 27, 2013

(65) Prior Publication Data
US 2015/0246150 A1 Sep. 3, 2015

(51) Int. Cl.
*A61L 2/22* (2006.01)
*A01N 25/06* (2006.01)
(Continued)

(52) U.S. Cl.
CPC .............. *A61L 2/22* (2013.01); *A01N 25/00* (2013.01); *A01N 25/06* (2013.01); *A01N 59/00* (2013.01);
(Continued)

(58) Field of Classification Search
CPC ........................................................ A61L 2/22
See application file for complete search history.

(56) References Cited

U.S. PATENT DOCUMENTS

2009/0214502 A1* 8/2009 Gheshlaghi ............ A01N 63/00
424/93.462

FOREIGN PATENT DOCUMENTS

| EP | 0219220 A1 | 4/1987 |
| EP | 2329893 A1 | 6/2011 |
| WO | WO-2006016558 | 2/2006 |

OTHER PUBLICATIONS

Todar. Structure and Function of Baterial Cells. Todar's Online Textbook of Bacteriology. 2012.*
(Continued)

*Primary Examiner* — Donald R Spamer
(74) *Attorney, Agent, or Firm* — Dinsmore & Shohl LLP

(57) ABSTRACT

Method for removing all types of particulate matter with exclusion of biological multiplying microorganisms in indoor environments characterized by comprising the following two steps:—the atomization of compounds that oxidize particulate matter to form complexes and to precipitate them;—the atomization of a liquid containing a mixture of spores of Gram-positive aerobic and/or of facultative anaerobic spore formers to act as nuclei for extra precipitation, to cover the precipitated particulate matter; and to metabolize precipitated particles and to take up precipitated particles by the Gram-positive bacteria/thereby preventing the precipitated particles to become airborne again;— whereby the drop size in both atomization steps is held between 5 and 50 μm to yield a dry nebula.

5 Claims, 2 Drawing Sheets

(51) Int. Cl.

| | |
|---|---|
| *A61L 2/18* | (2006.01) |
| *A61L 9/14* | (2006.01) |
| *C12N 1/00* | (2006.01) |
| *A01N 25/00* | (2006.01) |
| *A01N 59/00* | (2006.01) |
| *A01N 63/00* | (2006.01) |

(52) U.S. Cl.
CPC .............. *A01N 63/00* (2013.01); *A61L 2/186* (2013.01); *A61L 9/14* (2013.01); *C12N 1/005* (2013.01); *A61L 2202/25* (2013.01); *A61L 2209/211* (2013.01); *B01D 2251/106* (2013.01); *B01D 2257/91* (2013.01); *B01D 2259/10* (2013.01)

(56) References Cited

OTHER PUBLICATIONS

International Search Report dated Feb. 11, 2014, International Application No. PCT/BE2013/000033, filed Jun. 19, 2013.
"Preventing hospital infection from spreading-involves spraying with suspension of Bacillus pasteurii strain No. 119 to prolong disinfecting effect", DERWENT, Dec. 31, 1987, XP002196852, abstract.
Barlass, P. et al., Germination of Bacillus cereus spores in response to L-alanine and to inosine: the roles of gerL and gerQ operons, *Microbiology*, 148: 2089-95, 2002.
Bouillard, L. et al., Bacterial contamination of indoor air, surfaces, and settled dust, and related dust endotoxin concentrations in healthy office buildings, *Ann. Agric. Environ. Med.*, 12(2); 187-192, 2005.
Ghosh, S., Understanding the Mechanism of Bacillus Subtilis Spore Germination, Doctoral Dissertation, University of Connecticut, Nov. 13, 2013.
Gonzalez-Pastor, J., Cannibalism: a social behavior in sporulating Bacillus subtilis, *FEMS Microbiol. Rev.*, 35:415-424, 2010.
Kembel, S. et al., Architectural design influences the diversity and structure of the built environment microbiome, *The ISME Journal*, 6:1469-1479, 2012.
Meadow, J. et al., Indoor airborne bacterial communities are influenced by ventilation, occupancy, and outdoor air source, , Intl. J. of Indoor Environment and Health, 24: 41-48, 2014.
Pandey, R. et al., Live Cell Imaging of Germination and Outgrowth of Individual Bacillus subtilis Spores; the Effect of Heat Stress Quantitatively Analyzed with SporeTracker, PLOS One, 8(3): 1-10, e58972, Mar. 2013.
Vary, J. et al., Kinetics of Germination of Bacillus Spores, *Journal of Bacteriology*, 89(5): 1340-47, May 1965.
Verdonck, J., Bioaerosols to Improve the Indoor Air Quality, Master of Science Thesis, Catholic University of Louvain, Belgium, 2015.

\* cited by examiner

METHOD FOR REMOVING PARTICULATE MATTER IN INDOOR ENVIRONMENTS

The present invention relates to a method for removing particulate matter in indoor environments.

More specifically the invention is dedicated to sanitize rooms, spaces and installations in indoor environments that have been contaminated by present and former airborne particulate matter and its residues from external sources or from internal sources.

Particulate matter (PM) is an air pollutant comprising a mixture of solid and liquid particles suspended in the air. PM is largely composed of particles with an aerodynamic diameter (AD) of 10 μm or less. Fine particles have an aerodynamic diameter of 2.5 μm or less.

Airborne particles can be classified by size as follows:
TSP or Total Suspended Particulates, comprising all airborne particles (AD of 0.01 μm to 100 μm);
Coarse particles with an AD between 2.5 μm and 10 μm;
$PM_{10}$ or particles with an AD of less than 10 μm and are referred to as small particles;
$PM_{2.5}$ or particles with an AD of less than 2.5 μm, also referred to as fine particles;
$PM_{0.1}$ or particles with a diameter of less than 0.1 μm, also referred to as ultrafine particles.

The sources of particles can be roughly divided in three groups (www.rivm.nl, Handboek Binnenmilieu 2007):
Condensation of hot combustion products:ultra fine particles smaller than 0.1 μm;
Chemical reactions of air polluting gases in the atmosphere:fine particles between 0.1 μm and 2.5 μm;
Particles of mechanical origin such as wear, wind erosion, bulk transfer etc.: coarse particles of over 2.5 μm or small particles.

Particles can penetrate the respiratory system, the digestive system and even the blood stream. Damage to human health is caused mainly by the $PM_{2.5}$ fraction: these particles have the deepest penetration in the lungs and occur even in the blood or lymphatic system (WHO air quality and health fact sheet Nr. 313 September 2011).

In general, smaller particles ($PM_{10}$ and smaller) and combustion-related particles are more important for health effects than larger and mechanically-formed particles.

Outdoor sources of PM like transportation, industry or agriculture will define two thirds of the PM concentration indoors.

The main anthropogenic and biogenic sources of PM air pollutants in the interior of buildings are (WHO 2009, 2010, Indoor Air Quality Guidelines on dampness and moulds; WHO 2010, Indoor Air Quality Guidelines on selected pollutants; World Health Organisation):

a. from mankind:
tobacco smoke;
combustion processes: fireplaces, candles, fire;
cooking, baking and grilling;
vacuum cleaning;
carpets and upholstery;
phosphate from detergents;
human skin flakes;
residues of insecticide, pesticide, biocide such as deltamethrin, tetramethrin and permethrin and Persistent Organic Pollutants (POP) such as endosulfen, lindane, atrazine and DDT;
residues of cleaning agents and their odorants: limonene;
hazardous substances emitted from buildings, construction materials and indoor equipment: formaldehyde, acetaldehyde, trichloroethylene, tetrachloroethylene, phthalates, flame retardants (PBDEs, polybrominated diphenyl ethers), asbestos and man made mineral fibers (MMMF);
metals and metalloids: mercury (Hg), lead (pb), cadmium (Cd), tin (Ti) such as monobutyltin, dibutyltin, tributyltin, tetrabutyltin, monooctyltin, dioctyltin, tricyclohexyltin and triphenyltin, and arsenic (As);
organic solvents and other volatile organic compounds (VOC's).

b. from plants:
pollen and plant debris.

c. from bacteria:
endotoxins from cell lysis of Gram-negative bacteria, exotoxins.

d. from viruses, spores, fungi and algae:
biological aerosol particles with viruses, spores, fungi and algae.

e. from molds:
metabolites/excretion products of molds such as volatile organic components, allergens, proteins and enzymes, β (1-3)-glycans and mycotoxins (Demulle B., 2009, "Investigation of mycotoxin production in water-damaged mouldy interiors in connection with the sick building syndrome.", Ph.D. thesis Faculty Pharmacy University of Ghent);

A special case of arsenical poisoning in indoor environments is described by Bentley and Chasteen (2002) in "Microbial methylation of metalloids: Arsenic, Antimony and Bismuth" (Microbiology and Molecular Biology Reviews, June 2002, p 250-271) whereby the metalloids act as methyl group acceptors to produce volatile compounds by microorganisms.

f. from animals and pets such as cats, dogs, rabbits, birds:
excretions and allergens from skin flakes, feathers, urine, and saliva.

g. from dust mites:
allergens.

Traditionally such PM pollution in indoor environments is countered by dispensing ionized particles into the air by air cleaning devices built for this purpose.

The ionized negatively charged particles serve as nuclei onto which contaminating particles are attracted, causing them to precipitate.

Although some relief is obtained by such ionizers, they are not capable of cleaning indoor environments that are heavily contaminated, neither of removing the residual particulate matter itself.

A specific source of a combustion process is a fire in a building. After a fire has raged in rooms and ventilation systems within a building, these places and other areas become contaminated with PM due to air pressure differences created by the heat or by suction effects from ventilation shafts.

After a fire has raged, other buildings in the vicinity can be affected by the air contamination, and especially microbiological contamination can be a hazard if the nearby building is a hospital, where infections can occur caused by a fire in another building.

A specific case of particulate matter in indoor environments are volatile organic compounds from molds and bacteria in refrigerated spaces such as storage, transport and production of products at low temperatures. Some psychrotrophic microorganisms are adapted and capable of producing VOC's while growing at low temperature ranges from −1° C. to 18° C.

During scientific research at the university of Louvain (KULeuven) within a confidential project (IWT KMO innovatieproject 110273) entitled "nebulisation of healthy microorganisms in a cold environment ("vernevelen van gezonde micro-organismen in een koude omgeving") we were able to select, identify and characterize aerobic sporulating psychrotrophic bacteria from the genus *Sporosacrina*, (*Sporsarcina globispora, aquimarina, psychrophila*) *Paenisporosarsina* (*Paenisporosarsina macmoerdoensis*) and *Paenibacillus* (*Paenibacillus glacialis, amylolyticus, pabuli, xylanexedens, castaneae, macquariensis antarcticus*) with amylase, lipase, protease and nuclease activity at low temperatures to compete with biofilm forming microorganisms and production of effective antifungal components, tested against growth at low temperature of *Penicillium expansum* and *Aspergillus* spp.

It is a purpose of this invention to provide a method to treat indoor environments to remove effectively contamination of present and former airborne particulate matter and its residues with exclusion of biological multiplying microorganisms, and this at normal temperatures (18° C.-30° C.) and at lower temperatures (−1° C.-18° C.)

European Patent Application (EP 2.329.893) already describes a method for the microbiological cleaning of an interior space mentioning in the second paragraph that this invention is intended to clean an interior space that is biologically contaminated by viruses, bacteria, spores, yeast and molds and is characterized in that the method consist of a first step, being the automatic atomization of a biocide that decontaminates (destroys microorganisms) and a consecutive second step being the atomization of a benign biological culture of benign spore formers for biological stabilization, whereby the atomization in both steps delivers microdrops of 5 to 10 microns.

In paragraph 0049 it is mentioned that if odors are present that have a biological origin (transpiration odor, mold odor, urine odor), the combination of the first and second cleaning step will already deal with the microorganisms, that cause the odor change.

Also in claims 8 and 11 it is mentioned that if odors are present that are of non-biological origin such as smoke, fire odor, ashes of cigarettes) then a complex forming agent can be added to the benign biological solution in step II, based on surfactants (paragraph 0054). These surfactants seek out oily substances such as tar and isolate them by means of micelle formation with hydrophilic groups on the surface. This micelle lowers the surface tension of these oily substances with neutralization of the odor as a consequence.

To this end the present invention provides a method for removing particulate matter in indoor environments comprising the following two steps:
  the atomization of compounds that oxidize particulate matter, to form complexes and to precipitate them;
  the atomization of a liquid containing a mixture of spores of Gram-positive aerobic and/or of facultative anaerobic spore formers to act as nuclei for extra precipitation, to cover the precipitated particulate matter, and to metabolize precipitated particles and to take up precipitated particles by Gram-positive bacteria, thereby preventing the precipitated particles to become airborne again.

The drop size in both atomization steps is held between 5 and 50 μm to yield a dry nebula.

In case the PM is no longer airborne, but is precipitated already, this method can also be applied, since the second step will metabolize and take up the already precipitated particles by all means.

This second step intends to suppress after metabolising and taking up PM residues, the development of molds by outcompeting them with benign bacteria, thereby preventing the PM residues to become airborne again.

An advantage of this method to treat indoor environments is that it is aimed at preventing an explosion of mold growth after e.g. a fire, which has been overlooked so far.

Another advantage is that hydrophobic particles will be transformed by oxidation into hydrophilic particles, which thus can form complexes that can precipitate.

Another advantage is that the drop size of the atomization steps is such that on the one hand the drops are falling sufficiently rapidly while on the other hand they are whirled up sufficiently to reach all horizontal and vertical surfaces in the interior space.

An advantage of this method is also that the chemical first step is followed shortly thereafter by the second step thereby cleaning the interior air and enabling people to enter the interior space within one hour after the start of the treatment.

This can be achieved because residues of the oxidizing compounds of the first step are neutralized by the microbiological second step.

Another advantage of this method is that in the second step only spores of living microorganisms are used, thereby obviating the use of living organisms and the potential allergic reactions to these organisms.

Another advantage of this method is that it can be carried out in a fully automated way, whereby human intervention is not needed during the treatment.

Preferably the oxidizing compounds that oxidize particulate matter are peroxides such as hydrogen peroxide and peracetic acid or a mixture of ethanol and o./p.-t.Bu-cyclohexylacetate and fixolide.

An advantage of using peroxides as oxidizing compounds is that peroxides only leave oxygen and water as reaction products.

A typical composition of the oxidizing compounds solution is:
  Ethanol: 10-15 vol %;
  o.t.Bu-cyclohexylacetate: 0.1 to 1 vol %;
  p.t.Bu-cyclohexylacetate: 0.1 to 1 vol %;
  Fixolide: less than 0.1 vol %

Fixolide is a bicyclic compound having the CAS Reg. Nr. 1506-02-1, and is registered in Europe as EC 216-133-4.

Preferably, the spores of Gram-positive aerobic and/or the facultative anaerobic spore formers are members of the *Bacillus* species, such as *Bacillus subtilis, Bacillus amyloliquefaciens, Bacillus purailus, Bacillus licheniformis* and *Bacillus megaterium*.

For low temperature applications, spores of *Sporosarcina, Paenisporosarcina* and *Paenibacillus* species are preferred.

An advantage of this low temperature application is that biological displacement is also possible at these lower temperatures.

Another advantage is that spores serve as nuclei adhering oxidized particles to their surface and precipitating them.

An advantage of these benign microorganisms is that they can displace molds and thereby prevent explosive growth of molds after a e.g. a fire has occurred, and this in a sustainable way without the need for additional aggressive and toxic chemicals to be applied.

Another advantage of this method is that the benign microorganisms will metabolize particulate matter so that they will not become airborne again.

Another advantage of this method is that the spores of Gram-positive bacteria outgrow the growth of molds and thereby preventing an explosive growth of molds and production of particulate matter such as mycotoxins, VOC's, allergens, and β-glycans.

With the intention of better showing the characteristics of the invention, hereafter, as an example without any limitative character, a preferred form of embodiment is described of an improved device, with reference to the accompanying drawings, wherein:

FIG. 1 schematically represents the first step of the method of the invention;

FIG. 2 schematically represents the second step of the method of the invention;

Figure 1:
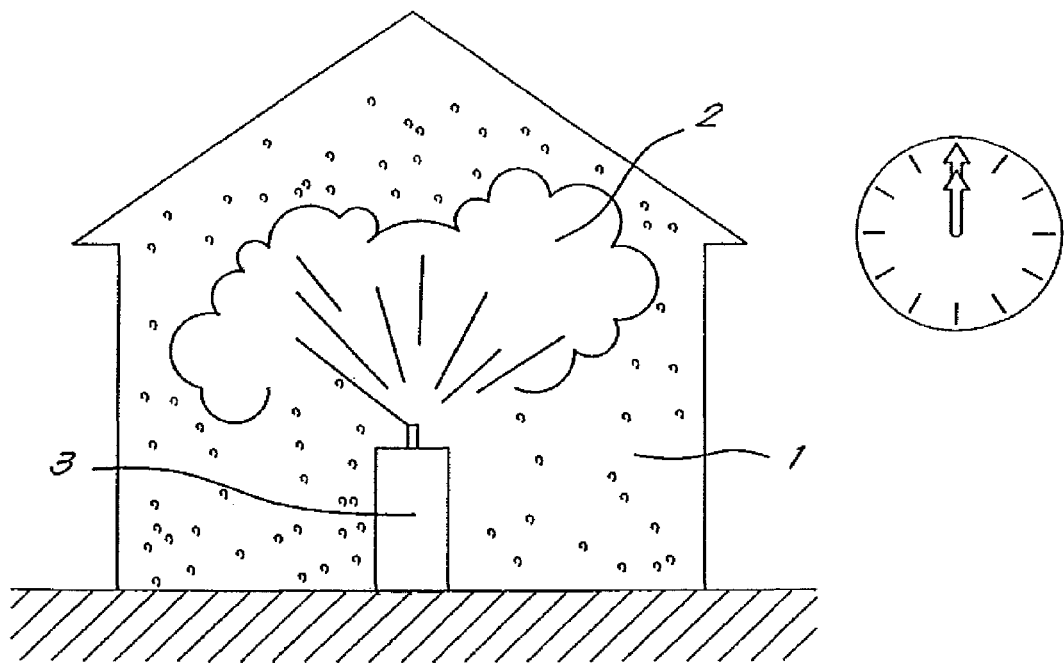

FIG. 1 represents the first step of treatment of the interior space 1 by the atomization of an oxidizing compound 2, by means of an atomizer 3.

Figure 2:
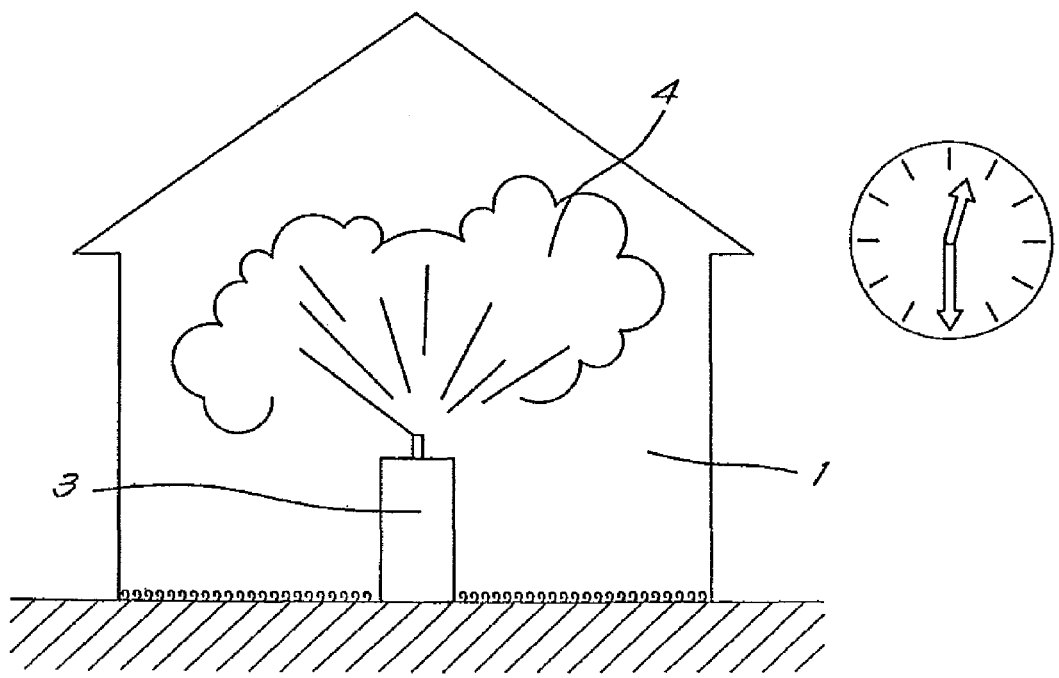

FIG. 2 represents the second step of treatment of the interior space 1 after less than an hour, whereby a benign biological culture 4 of spores of type Gram-positive aerobic spore formers such as *Bacillus* species and/or spores of *Sporosarcina, Paenisporosarcina* and *Paenibacillus* species is also atomized in the same indoor environment.

Figure 3:
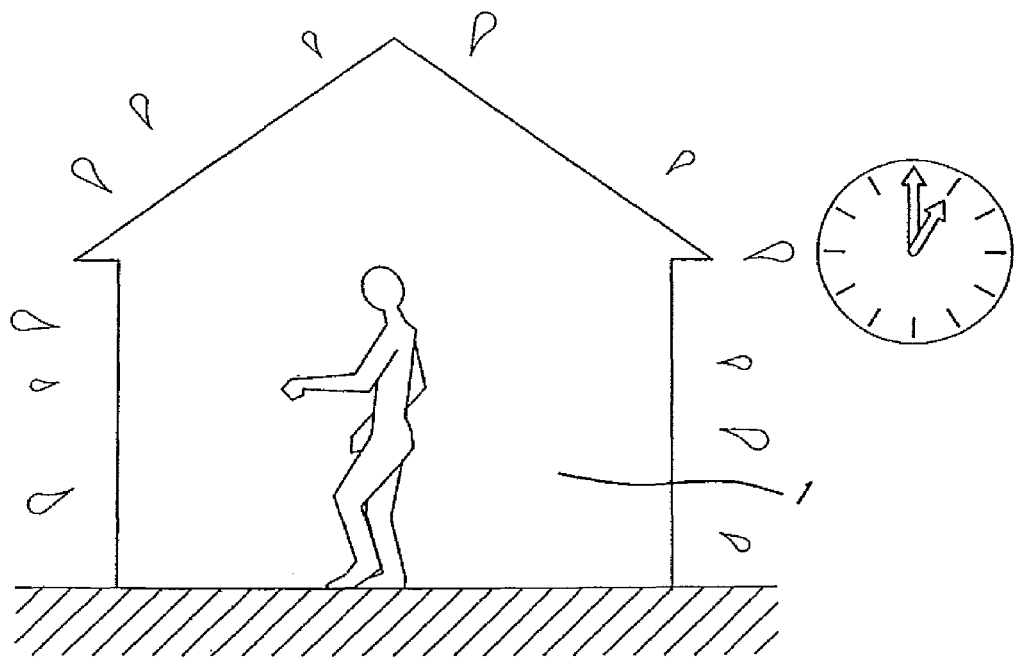
FIG. 3 represents the interior space after cleaning.

FIG. 3 shows the cleaned space after the two treatment steps whereby the interior space is again accessible to inhabitants one hour after the treatment has started.

Figure 4:
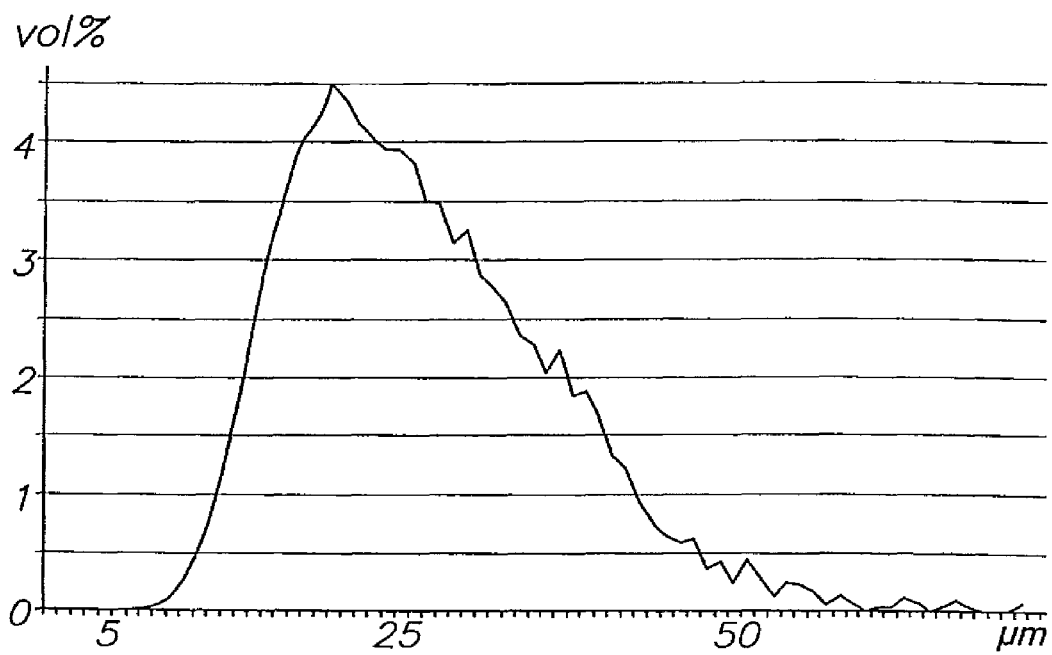
FIG. 4 represents the drop size distribution of the microdrops generated by the method of this invention.

FIG. 4 shows the distribution of the volumetric size of the microdrops generated by the atomization steps in the method of this invention in an indoor environment. Almost all the drops are sized between 5 and 50 micrometers.

The method of this invention works by, in a first step, atomizing a solution of oxidizing compounds of which an atomizer produces small nebula drops sized between 5 to 50 micrometer.

The droplets spread in the air of the interior space and on all surfaces of it, thereby washing the air itself from particulate matter flowing in the air and oxidizing the particulate matter on the surfaces in order to oxidize particulate matter to form complexes and to precipitate them.

In a second step, a solution is atomized containing spores of Gram-positive spore formers 4, such as *Bacillus* species, and/or spores of *Sporosarcina, Paenisporosarcina* and *Paenibacillus* species with the following effect:

the reduction of the remaining oxidizing agent from the first step by neutralisation;

the homogeneous spreading of the spores of Gram-positive spore formers and/or spores of *Sporosarcina, Paenisporosarcina* and *Paenibacillus* through the atomization in the interior space;

the spores of Gram-positive bacteria outgrowing the growth of molds thereby preventing an explosive growth of molds, and creating a stable and healthy microflora;

the growth of Gram-positive microorganisms will outgrow the growth of Gram-negative bacteria thereby preventing the production of endotoxins and exotoxins within the indoor environment.

at low temperature, specific species of *Sporosarcina, Painsporosarcina* and *Paenibacillus* species outcompeting biofilm forming microorganisms through high amylase, protease, lipase and nuclease activity and production of antifungal components against molds;

the spores of Gram-positive bacteria metabolizing precipitated particles and taking up precipitated particles, thereby preventing the precipitated particles to become airborne again.

The treatment of the indoor environment is finished within one hour, making the interior space accessible to unprotected persons within a short time.

An advantage of the method is therefore that the affected rooms or interior spaces can be released very quickly for reoccupation, without the use of traditional cleaning techniques which are inappropriate and ineffective.

The present invention is in no way limited to the form of embodiment described by way of an example and represented in the figures, however, such an improved invention for treating building interiors after contamination with particulate matter can be realized in various forms without leaving the scope of the invention.

The invention claimed is:

1. A method for treatment of an indoor environment by removing precipitated particulate matter consisting of:

atomizing a liquid containing a mixture of spores of Gram-positive aerobic spore formers to act as nuclei for extra precipitation, to cover the precipitated particulate matter; and to metabolize the precipitated particulate matter and to take up the precipitated particulate matter by Gram-positive bacteria, thereby preventing the precipitated particulate matter from becoming airborne again; the atomizing thus producing an atomized liquid having a drop size wherein the drop size of the atomized liquid is held between 5 and 50 pm to yield a dry nebula.

2. The method according to claim 1, wherein the Gram-positive aerobic spore formers are members of the *Bacillus* genus.

3. The method according to claim 1, wherein the atomizing is carried out at a low temperature between −1° C. and 18° C., and wherein the spore formers are members of a genus selected from the group consisting of: *Sporosarcina, Paenisporosarcina* and *Paenibacillus*.

4. The method according to claim 1, wherein the treatment of the indoor environment is finished within one hour, and makes the indoor environment accessible for unprotected persons after one hour.

5. The method according to claim 2, wherein the Gram-positive aerobic spore formers are selected from the group consisting of: *Bacillus subtilis, Bacillus amyloliquefaciens, Bacillus pumilus, Bacillus licheniformis* and *Bacillus megaterium*.

* * * * *